(12) United States Patent
Spyrou et al.

(10) Patent No.: US 11,739,055 B2
(45) Date of Patent: Aug. 29, 2023

(54) PROCESS FOR PREPARING DIISOCYANATES BASED ON LYSINE

(71) Applicant: Evonik Operations GmbH, Essen (DE)

(72) Inventors: Emmanouil Spyrou, Schermbeck (DE); Holger Loesch, Herne (DE); Susanne Kreischer, Herten (DE); Andrea Diesveld, Gescher (DE); Andrea Thesing, Ahaus (DE); Jörg-Joachim Nitz, Essen (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/358,541

(22) Filed: Jun. 25, 2021

(65) Prior Publication Data

US 2021/0403417 A1   Dec. 30, 2021

(30) Foreign Application Priority Data

Jun. 26, 2020 (EP) .................................... 20182431

(51) Int. Cl.
*C07C 263/06* (2006.01)
*C07C 269/04* (2006.01)

(52) U.S. Cl.
CPC .......... *C07C 263/06* (2013.01); *C07C 269/04* (2013.01)

(58) Field of Classification Search
CPC ... C07C 263/06; C07C 269/04; C07C 263/04; C07C 265/14; C07C 269/00; C07C 271/22; C07C 273/1863; C07C 275/16
See application file for complete search history.

(56) References Cited

U.S. PATENT DOCUMENTS

2020/0048403 A1    2/2020  Miyake et al.
2020/0115327 A1*   4/2020  Miyake ................ C07D 233/64

FOREIGN PATENT DOCUMENTS

GB            965474  *  7/1964
WO    WO2018/212208  * 11/2018

OTHER PUBLICATIONS

Gonko et al., "Synthesis and investigation of α-nitrosoureidocarbonic acids with potential antitumor activity," Pharmaceutical Chemistry Journal, (1978), 12(5):601-606.
European Patent Office Extended Search Report for Application No. 20182431.5 dated Dec. 10, 2020 (9 pages statement of relevance included).

* cited by examiner

*Primary Examiner* — Jafar F Parsa
*Assistant Examiner* — Blaine G Doletski
(74) *Attorney, Agent, or Firm* — Michael Best & Friedrich LLP

(57) ABSTRACT

The invention relates to a process for preparing a diisocyanate of the formula (A)

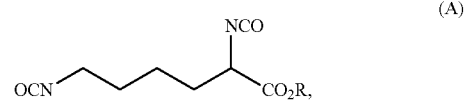

where R is selected from the group consisting of alkyl, aryl, and combinations thereof, comprising the following process steps in the indicated order;
1) providing an intermediate of the formula (B) with a process using lysine and urea

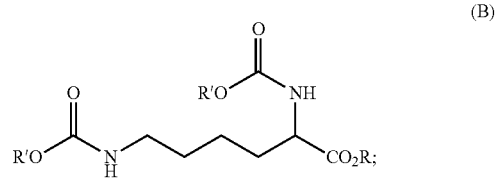

and
where R and each R' are independently selected from the group consisting of alkyl, aryl, and combinations thereof; and
2) thermolytic cleavage of the intermediate of the formula (B),
thereby affording the diisocyanate of the formula (A), and also to the diisocyanate directly prepared therewith.

20 Claims, No Drawings

PROCESS FOR PREPARING DIISOCYANATES BASED ON LYSINE

CROSS REFERENCE TO RELATED APPLICATION

This patent application claims priority to European Application No. 01824315, filed Jun. 26, 2020, the entire contents of which is hereby incorporated by reference.

The present invention relates to a process for preparing diisocyanates and to the diisocyanate prepared therewith.

BACKGROUND OF THE INVENTION

Diisocyanates based on lysine (also referred to in the prior art as "lysine diisocyanate esters") are known compounds and are used primarily for medicinal applications. Various processes for preparing these compounds are disclosed in the prior art.

EP 3 527 593 A1 teaches a process for the preparation thereof using phosgene. The pronounced toxicity of this compound necessitates laborious and costly safety precautions during storage and production. In addition to the safety and environmental aspects, such laborious and costly safety precautions are also undesirable, since they ultimately make the process less cost-efficient. Common alternatives to phosgene, for example triphosgene, likewise have similar toxicity. The above-mentioned considerations accordingly apply to these compounds too and to processes that employ them.

EP 3 626 705 A1 discloses a process that can be used to produce inter alia lysine diisocyanate esters through thermal decomposition of a carbamate. The corresponding carbamates are however initially costly to produce. The lysine carbamate used in the examples must for example be laboriously produced from the—in some cases poorly accessible—compounds diphenyl carbonate, tri-ethylamine and lysine β-aminoethyl ester trihydrochloride.

Other processes of the prior art have the additional disadvantage that the diisocyanates have undesirable colours. The removal of these colours necessitates laborious purification processes, rendering such processes no longer cost-efficient.

OBJECT OF THE INVENTION

The known processes of the prior art have inter alia the disadvantage of using compounds that are highly toxic and ecologically harmful. This is however incompatible with the demands of a more sustainable economy.

There is therefore a need to overcome the disadvantages of the prior art and to provide an improved process for preparing diisocyanates of the formula (A). Such improvements are aimed in particular at improving process control, improving environmental compatibility and reducing the risks to health of the process. The process should also ideally be made simpler, particularly with regard to the safety requirements necessary for its performance. Finally, it is also desirable to improve the cost efficiency of the process, for example by using simpler equipment or by avoiding laborious purification processes.

SUMMARY OF THE INVENTION

The objects of the present invention are achieved by the process according to the invention for preparing a diisocyanate of the formula (A)

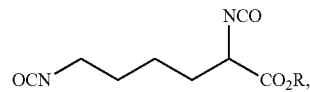

where R is selected from the group consisting of alkyl, aryl, and combinations thereof, comprising the following process steps in the indicated order:
1) providing an intermediate of the formula (B) with a process using lysine and urea

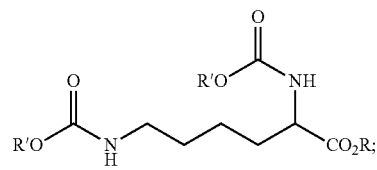

where R and each R' are independently selected from the group consisting of alkyl, aryl, and combinations thereof; and
2) thermolytic cleavage of the intermediate of the formula (B),
thereby affording the diisocyanate of the formula (A).

DESCRIPTION OF THE INVENTION

Percentages in the description and in the claims are percent by weight (abbreviated as % by weight), unless otherwise specified. Yields are stated as percentages of the theoretical yield. The various embodiments described hereinbelow can be combined with one another where this is technically possible and nothing to the contrary is specified. The terms "conversion" and "reaction" are used synonymously, as is usual in the prior art.

For the purposes of the present invention, the term "alkyl" comprises branched and unbranched alkyl groups including cyclic and/or acyclic structural elements, cyclic structural elements comprising by definition at least three carbon atoms. C1-CX alkyl in the description and in the claims refers to alkyl groups comprising 1 to X carbon atoms (X is a natural number). C1-C8 alkyl includes, for example, methyl, ethyl, n-propyl, isopropyl, n-butyl, isobutyl, sec-butyl, tort-butyl, n-pentyl, isopentyl, sec-pentyl, tert-pentyl, neopentyl, hexyl, heptyl and octyl.

For the purposes of the present invention, the term "aryl" comprises cyclic aromatic molecular fragments (or groups), for example phenyl or naphthyl, in which one or more of the carbon atoms forming the ring can be replaced by N, O and/or S, such as in pyridyl for example. Preferably, none of the carbon atoms forming the ring are substituted by N, O and/or S.

Combinations of alkyl and aryl are for the purposes of the invention molecular fragments that comprise at least one alkyl group and at least one aryl group, for example benzyl and tolyl.

Optionally, alkyl and aryl are functionalized, Functionalization is the formal replacement of a hydrogen atom in said group by a functional group, preferably by hydroxy (—OH) and/or amino (—NH$_2$) groups.

Where more than one radical needs to be selected for a compound named in the claims or in the description, said radicals are selected independently of one another, irrespective of whether selection is from one list or from a plurality thereof. They may, if the lists provide for this, therefore be the same or different.

Where the quantifier "one" is used in the claims or in the description (for example "a/one diisocyanate" or "an/one alcohol"), this is to be generally understood as meaning "at least one" (for example "at least one diisocyanate" or "at least one alcohol"), i.e. one or more than one. To improve readability, this wording has not been used.

The process according to the invention is suitable for preparing a diisocyanate of the formula (A)

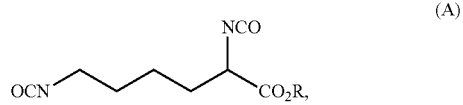

where R is selected from the group consisting of alkyl, aryl, and combinations thereof, R is preferably selected from the group consisting of C1-C8 alkyl, more preferably from methyl, ethyl, isopropyl, n-propyl, n-butyl, isobutyl, sec-butyl and tert-butyl, in particular from methyl, ethyl and n-butyl.

Very particularly preferred diisocyanates of the formula (A) are for the purposes of the invention the following racemic mixtures and following corresponding L-enantiomers:
the methyl ester (CAS No. 4460-02-0 in the form of the racemic mixture, CAS No. 45158-78-9 as the L-form), the ethyl ester (CAS No. 4254-76-6 in the form of the racemic mixture, CAS No. 45172-15-4 as the L-form) and the butyl ester (24305-78-0 in the form of the racemic mixture, CAS No. 1291098-99-1 as the L-form). These very particularly preferred diisocyanates are of exceptional economic importance.

The process according to the invention comprises at least process steps 1) and 2). The process according to the invention optionally includes further process steps that can be carried out before, during, between and/or after process steps 1) and 2).

Process step 1) provides the intermediate of the formula (B)

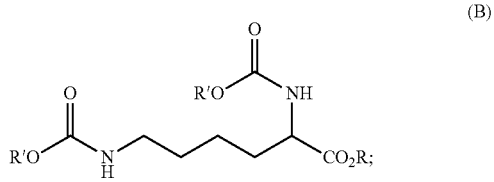

where R and each R' are independently selected from the group consisting of alkyl, aryl, and combinations thereof, with a process using lysine and urea.

A process using lysine and urea is understood as meaning here a process in which lysine, urea, at least one alcohol and optionally at least one base and/or at least one acid are reacted together.

In the preferred procedure for this, either i) lysine and urea are reacted and the resulting urea adduct reacts further with an alcohol to the intermediate (8) or ii) an initial charge of lysine is reacted with a base to form a carboxylate salt and the carboxylate salt is reacted with urea to form a urea salt that is reacted with an alcohol to form intermediate (B) either ii) a) directly or ii) b) after an intermediate reaction with acid back to the carboxylic acid.

R and R' are preferably selected from the group consisting of C1-C8 alkyl, more preferably from methyl, ethyl, isopropyl, n-propyl, n-butyl, isobutyl, sec-butyl and tert-butyl, in particular from methyl, ethyl and n-butyl.

The intermediate of the formula (B) can also be initially charged, and thus provided, in a suitable reaction vessel. Processes for preparing the intermediate of the formula (B) are known in the prior art.

In process step 2), the intermediate of the formula (B) undergoes thermolytic cleavage. This affords the diisocyanate of the formula (A). The thermolytic cleavage is preferably mediated by a mediator, more preferably by a metal-based catalyst, even more preferably by a tin(II) salt. Particular preference is given to using a tin(II) halide such as tin(II) chloride or tin(II) bromide. A mediator is for the purposes of the invention a compound that either enables or ideally accelerates the thermolytic cleavage. A catalyst is for the purposes of the invention a compound that either enables or ideally accelerates the thermolytic cleavage and can be used in substoichiometric amounts based on the reactants (in the present case the intermediate of the formula (B)).

The thermolytic cleavage is optionally carried out in a solvent. This optional solvent is selected from the group consisting of aprotic solvents. The optional solvent is preferably anhydrous. This means that the concentration of water in the solvent is not more than 1% by weight, preferably not more than 0.1% by weight, more preferably not more than 0.01% by weight. The optional solvent is preferably high-boiling, i.e. having a boiling point of preferably at least 200° C., more preferably at least 250° C. A preferred example is Marlotherm SH. Solvents optionally present and other volatile constituents are removed before the start of the thermolytic cleavage, for example by distillation.

The temperature during the thermolytic cleavage is preferably within a range from 160 to 240° C., more preferably within a range from 170 to 230° C., in particular within a range from 180 to 220° C. The diisocyanate formed is preferably distilled out of the reaction vessel continuously during the reaction.

The duration of the thermolytic cleavage reaction depends on various parameters and can be chosen as appropriate by those skilled in the art.

In a first preferred embodiment, the intermediate of the formula (B) is obtained by the following process steps (hereinafter referred to as "variant 1"):
a.1) providing of lysine;
a.2) reacting the lysine with urea to form a urea adduct of the formula (C)

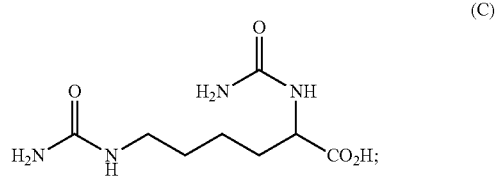

and
a.3) reacting the urea adduct of the formula (C) with an alcohol to form the intermediate of the formula (B).

In a second preferred embodiment, the intermediate of the formula (B) is obtained by the following process steps (hereinafter referred to as "variant 2"):

b.1) providing of lysine;
b.2) reacting the lysine with a base to form a lysine salt of the formula (Z)

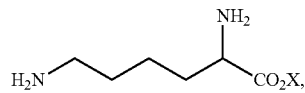
(Z)

where X is a counterion;
b.3) reacting the lysine salt of the formula (Z) with urea to form a urea salt of the formula (Y);

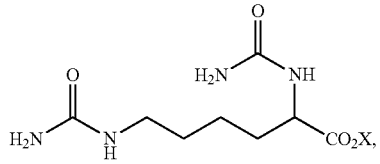
(Y)

where X is a counterion;
b.4) reacting the urea salt of the formula (Y) with an alcohol to form a carbamate of the formula (X)

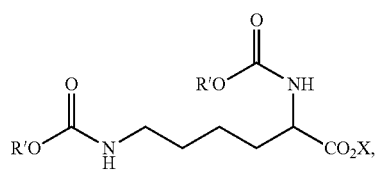
(X)

where each R' is independently selected from the group consisting of alkyl, aryl, and combinations thereof, and
X is a counterion;
b.5) reacting the carbamate of the formula (X) with an acid to form the carboxylic acid of the formula (W)

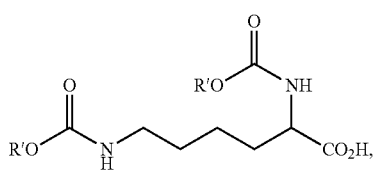
(W)

where each R' is independently selected from the group consisting of alkyl, aryl, and combinations thereof, and
b.6) reacting the carboxylic acid of the formula (V with an alcohol to form the intermediate of the formula (B).

In a third preferred embodiment, the intermediate of the formula (B) is obtained by the following process steps (hereinafter referred to as "variant 3"):

c.1) providing of lysine;
c.2) reacting the lysine with a base to form a lysine salt of the formula (Z);

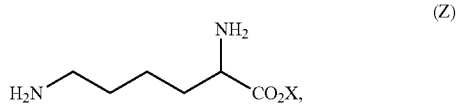
(Z)

where X is a counterion;
c.3) reacting the lysine salt of the formula (Z) with urea to form a urea salt of the formula (Y);

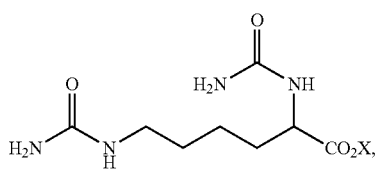
(Y)

where X is a counterion;
c.4) reacting the urea salt of the formula (Y) with an alcohol to form the intermediate of the formula (B), optionally with prior protonation of the carboxylate salt.

Variant 1 advantageously involves very few reaction steps and is therefore, and on account of the yields achievable in the individual process steps, cost-efficient.

Variant 2 allows the selective introduction of a wide range of different options for the radical R. For example, it also allows the incorporation of higher-molecular-weight radicals into the diisocyanate, which otherwise could cause problems in the thermolytic cleavage of the intermediate of the formula (B), since otherwise all radicals R and R' in the intermediate of the formula (B) are normally identical. Variant 3 achieves lower by-product formation, although the salt formed as a side product needs to be removed. Preferably, variant 1 or variant 2 is used. More preferably, variant 1 is used.

Variants 1, 2 and 3 are used to provide the intermediate of the formula (B). These variants can thus supplement/precede process step 1).

In process steps a.1), b.1) and c.1), lysine is provided. This is for example initially charged in a suitable reaction vessel or it is added to an appropriate reaction mixture. Lysine is used here in the form of L-lysine, R-lysine or as a mixture thereof (e.g. in the form of the racemate).

In process steps a.2), b.3) and c.3), lysine reacts with urea to form a urea adduct of the formula (C), or the lysine salt of the formula (Z) reacts with urea to form a urea salt of the formula (Y).

The molar ratio of the urea (in process steps a.2), b.3) and c.3)) is preferably within a range from 1:1 to 5:1 based on the primary amine groups of the lysine or of the lysine salt of the formula (Z). This means that the calculated amount of urea used is 1 to 5 molecules per primary amine group of the lysine or of the lysine salt. This allows optimal yields of the desired reaction products to be obtained. More preferably, the molar ratio is within a range from 1.25:1 to 3:1 and even more preferably within a range from 1.4:1 to 2.5:1.

Preferably, the reaction in process steps a.2), b.3) and c.3) is carried out in a polar solvent, more particularly in water on account of its dissolution properties and advantageous ecological characteristics.

The reaction in process steps a.2), b.3) and c.3) is preferably carried out at a temperature from 50 to 120° C., more preferably from 30 to 110° C.

The reaction is typically carried out until complete conversion of at least one of the reactants, usually the lysine or the lysine salt of the formula (Z). Those skilled in the art can check this by standard methods of analysis, e.g. by gas chromatography. The end of ammonia evolution (detectable for example by a moist pH paper in the offgas) can likewise serve as a method for determining when the reaction has gone to completion. The duration of the reaction depends on various parameters, for example temperature. Reaction times commonly range from 10 min to 1200 min, preferably 60 to 600 min, more preferably 120 to 420 min.

In process steps a.3), b.6) and c.4), the intermediate of the formula (B) is formed from the urea adduct of the formula (C), from the carboxylic acid of the formula (W) or from the urea salt of the formula (Y), through reaction with an alcohol.

The alcohol is for the purposes of the invention an organic compound having at least one, preferably (only) one, hydroxy group. It comprises either an alkyl group, an aryl group or combinations thereof on which is attached at least one hydroxy group. The alcohol is preferably selected from the group consisting of C1-C8 alcohol, more preferably from the group consisting of methanol, ethanol, isopropanol, n-propanol, n-butyl, isobutanol, sec-butanol and tert-butanol.

In order to ensure that the urea adduct of the formula (C), carboxylic acid of the formula (W) or urea salt of the formula (Y) react swiftly and as quantitatively as possible, the one alcohol is used in a stoichiometric excess based on said components. More preferably, the molar ratio of the one alcohol based on the urea adduct of the formula (C), carboxylic acid of the formula (W) or urea salt of the formula (Y) is within a range from 2:1 to 100:1. Even more preferably, the molar ratio is within a range from 5:1 to 50:1, ideally within a range from 10:1 to 25:1. When more than one alcohol is used, the sum of all the molar amounts of the alcohols is within the specified ranges.

The pressure during the reaction with the alcohol in process step a.3), b.6), c.4) is preferably for at least part of the time within a range from ≥1 bar, preferably within a range from 1 to 35 bar, more preferably within a range from 1 to 25 bar.

The pressure during the reaction with the alcohol in process step a.3), b.6), c.4) is within the specified range for preferably 1 to 20 hours, more preferably for 3 to 10 hours, in particular for 4 to 6 hours.

The reaction with the alcohol in process step a.3), b.6), c.4) is preferably carried out at a temperature within a range from 150 to 300° C., preferably at a temperature from 180 to 230° C., more preferably at a temperature from 190 to 220° C. In principle, excessively high temperatures in the process according to the invention can in unfavourable cases cause a reduction in yield due to decarboxylation or similar decomposition reactions. If the temperature is too low, disadvantageous long reaction times may be necessary in order to achieve good yields.

The reaction in process step a.3), b.6), c.4) is typically conducted until conversion of the urea adduct of the formula (C), of the carboxylic acid of the formula (W) or of the urea salt of the formula (Y) is as complete as possible. For this, the reaction with the alcohol in process step a.3), b.6), c.4) is conducted within the specified temperature range for a period preferably of 1 to 20 hours, preferably of 3 to 10 hours, in particular of 4 to 6 hours. Reaction times outside those specified may also be advantageous, depending on the reaction kinetics in the particular case, An esterification catalyst may optionally be used in process step a.3), b.6), c.4). Suitable esterification catalysts are known to those skilled in the art. For example, acids such as sulfuric acid, methanesulfonic acid or phosphoric acid, or metal-organic compounds such as common tin or titanium salts, may be used.

In process step b.2) and c.2), lysine reacts with a base to form a lysine salt of the formula (Z). The base (in process step b.2) and c.2)) is not further restricted. Any base that is suitable for removing the proton of the lysine and suitable for forming a lysine salt of the formula (Z) may be used. Numerous suitable bases are known to those skilled in the art. Particularly suitable bases are metal hydroxides (in particular alkali metal hydroxides such as lithium hydroxide, sodium hydroxide or potassium hydroxide), amines and ammonia.

X (in the formula (Z)) is a counterion, X results from the base used. X is preferably from the group consisting of alkali metal ion (in particular lithium, sodium and potassium ions) and ammonium ion. If X has a plurality of positive charges, it will accordingly be bound to more than one lysine anion, e.g. in $Mg(Lys)_2$.

The base in process step b.2) and c.2) is typically used in a molar ratio of at least 1:1 based on the lysine. The amount of base required depends inter alia on the base strength thereof. It is used preferably in a molar ratio of 1.1:1, more preferably in a molar ratio of 1.05:1, based on the lysine used.

Optionally, the reaction of the lysine with a base to form a lysine salt of the formula (Z) in process step b.2) and c.2) is carried out in a polar solvent. Suitable solvents are selected from the group consisting of water, tetrahydrofuran (THF), dioxane and N,N-dimethylformamide (DMF) and mixtures thereof. Particular preference is given to water, for the reasons cited above.

The reaction of the lysine with a base to form a lysine salt of the formula (Z) in process step b.2) or c.2) is preferably carried out at a temperature within a range from 0 to 50° C., preferably at a temperature from 20 to 30° C., more preferably at a temperature from 20 to 25° C.

The reaction of the lysine with a base to form a lysine salt of the formula (Z) (in process step b.2) and c.2)) is typically conducted until conversion of the lysine is as complete as possible. Typical reaction times are within a range from 1 second to 3 hours, preferably within a range from 0.1 to 1 hours. The reaction generally takes place without delay (acid-base reaction). The reaction time is limited only by the exothermicity that develops.

In process step b.4), the urea salt of the formula (Y) reacts with an alcohol to form a carbamate of the formula (X).

For details and selection options as regards the alcohol, the molar ratio of alcohol to urea salt of the formula (Y), the reaction conditions (pressure, temperature, reaction time and optional use of an esterification catalyst), the same information as for process steps a.3), b.6), c.4) applies.

In an embodiment of the present invention, the alcohols used in process step b.4) and in process step b.6) are different. The alcohol used in process step b.4) is then selected from the group consisting of methanol, ethanol and butanol, and the alcohol used in process step b.6) from the group consisting of methanol, ethanol and butanol. This embodiment can also be used to introduce otherwise inaccessible ester groups into the diisocyanate, for example esters starting from alcohols when they are attached to the carbamate groups, which could interfere with the thermolytic cleavage of the corresponding intermediate of the formula (B).

In process step b.5), the carbamate of the formula (X) reacts to form the carboxylic acid of the formula (W). The acid (in process step b.5)) is not further restricted. Any acid that is suitable for forming the carboxylic acid of the formula (W) from the carbamate of the formula (X) may be used in accordance with the invention. Numerous suitable acids are known to those skilled in the art. The acid is preferably selected from mineral acids (preferably sulfuric acid, hydrochloric acid, phosphoric acid) and organic acids (for example methanesulfonic acid and citric acid). Hydrochloric acid is particularly preferred.

The acid (in process step b.5)) is typically used in a molar ratio of at least 1:1 based on the carbamate of the formula (X). The amount of acid required depends inter alia on the acid strength thereof. It is used preferably in a molar ratio of 1.2:1, more preferably in a molar ratio of 1.05:1, based on the carbamate of the formula (X) used.

Optionally, the reaction of the carbamate of the formula (X) with an acid to form a carboxylic acid of the formula (W) in process step b.5) is carried out in a polar solvent. Suitable solvents are selected from the group consisting of water, tetrahydrofuran (THF), dioxane and N,N-dimethylformamide (DMF) and mixtures thereof. Particular preference is given to water, for the reasons cited above.

The reaction of the carbamate of the formula (X) with an acid to form a carboxylic acid of the formula (W) in process step b.5) is preferably carried out at a temperature within a range from 0 to 50° C., preferably at a temperature from 20 to 30° C., more preferably at a temperature from 20 to 25° C. Any exothermicity that develops can be absorbed by cooling.

The reaction of the carbamate of the formula (X) with an acid to form a carboxylic acid of the formula (V (in process step b.5)) is typically conducted until conversion of the carbamate of the formula (X) is as complete as possible. Typical reaction times are within a range from 1 second to 1 hour, preferably within a range from 0.1 to 0.5 hours.

In process step c.4), the urea salt of the formula (Y) reacts with an alcohol to form the intermediate of the formula (8). A mediator may optionally be used here, which is not further restricted. The mediator typically has acidic or water-attracting properties. Any mediator that is suitable for mediating the reaction of the urea salt of the formula (Y) with an alcohol to form the intermediate of the formula (8) may be used. Numerous suitable options are known to those skilled in the art. Examples that may be used include acidic molecular sieves, strong mineral acids (preferably sulfuric acid, hydrochloric acid, phosphoric acid) and strong organic acids (for example methanesulfonic acid). Particularly advantageous here are acids selected from the group consisting of sulfuric acid, methanesulfonic acid, hydrochloric acid and mixtures thereof.

The mediator (in process step c.4)) is typically used in catalytic amounts based on the urea salt of the formula (Y). The amount of mediator required depends inter alia on the properties thereof. It is preferably used in amounts of 0.001% to 1% by weight based on the urea salt of the formula (Y).

Optionally, the reaction of the urea salt of the formula (Y) with an alcohol to form the intermediate of the formula (B) (in process step c.4)) is carried out in a polar solvent. Suitable solvents are selected from the group consisting of water, tetrahydrofuran (THF), dioxane and N,N-dimethylformamide (DMF) and mixtures thereof.

The reaction of the urea salt of the formula (Y) with an alcohol to form the intermediate of the formula (B) in process step c.4) is preferably carried out at a temperature within a range from 150 to 300° C., preferably at a temperature from 180 to 230° C., more preferably at a temperature from 190 to 220° C.

The reaction of the urea salt of the formula (Y) with an alcohol to form the intermediate of the formula (B) in process step c.4) is typically conducted until conversion of the urea salt of the formula (Y) is as complete as possible. Typical reaction times are within a range from 1 to 20 h, preferably from 3 to 10 h, in particular from 4 to 6 h.

The process preferably includes a further process step (3) after and/or during process step 2):

3) purifying the diisocyanate of the formula (A), preferably by fractional distillation. Particularly preferably, the diisocyanate is, at least during the thermolytic cleavage, purified by distillation, preferably by fractional distillation. This means that the diisocyanate is already being removed from the reaction mixture as it forms. This sometimes improves the reaction yield, in particular the space-time yield. In order to achieve an optimal yield, it can occasionally be necessary to carry out further purification, even after the thermolytic cleavage is complete.

The distillation is preferably carried out under reduced pressure. Preferred pressures for the distillation are within a range from 0.01 to 200 mbar, preferably within a range from 0.1 to 100 mbar, more preferably within a range from 1 to 50 mbar. Potentially thermally unstable diisocyanates are thus purified more gently, thereby improving the yield. Purification can alternatively also take place on completion of process step 2).

In a preferred embodiment, the process according to the invention for preparing a diisocyanate of the formula (A)

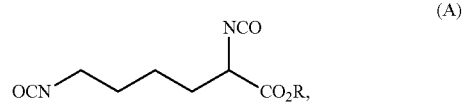
(A)

where R is selected from the group consisting of alkyl, aryl, and combinations thereof, comprises the following process steps in the indicated order:

a.1) providing of lysine;

a.2) reacting the lysine with urea to form a urea adduct of the formula (C)

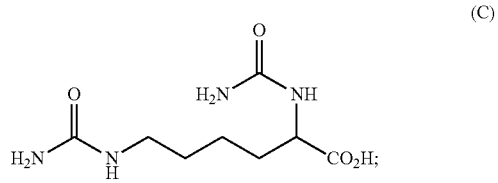 [SMILES: NC(=O)NCCCCC(NC(N)=O)C(=O)O]
(C)

and a.3) reacting the urea adduct of the formula (C) with an alcohol to form the intermediate of the formula (B);

or b.1) providing of lysine;

b.2) reacting the lysine with a base to form a lysine salt of the formula (Z);

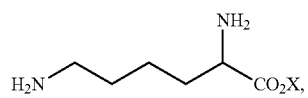

where X is a counterion;
b.3) reacting the lysine salt of the formula (Z) with urea to form a urea salt of the formula (Y);

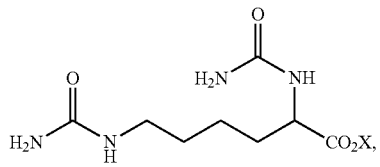

where X is a counterion;
b.4) reacting the urea salt of the formula (Y) with an alcohol to form a carbamate of the formula (X)

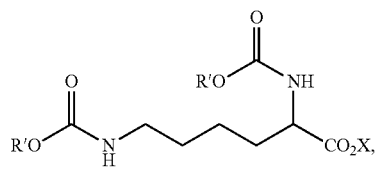

where each R' is independently selected from the group consisting of alkyl, aryl, and combinations thereof, and
X is a counterion;
b.5) reacting the carbamate of the formula (X) with an acid to form the carboxylic acid of the formula (W)

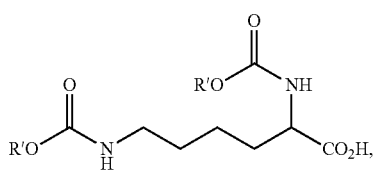

where each R' is independently selected from the group consisting of alkyl, aryl, and combinations thereof, and
b.6) reacting the carboxylic acid of the formula (W) with an alcohol to form the intermediate of the formula (B); or
c.1) providing of lysine;
c.2) reacting the lysine with a base to form a lysine salt of the formula (Z);

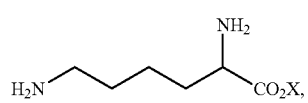

where X is a counterion;

c.3) reacting the lysine salt of the formula (Z) with urea to form a urea salt of the formula (Y);

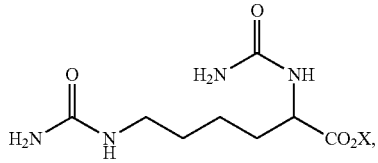

where X is a counterion;
c.4) reacting the urea salt of the formula (Y) with an alcohol to form the intermediate of the formula (B);
thereby providing the intermediate of the formula (B)

(B)

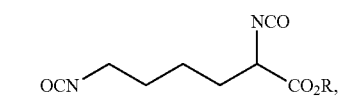

and
where R and each R' are independently selected from the group consisting of alkyl, aryl, and combinations thereof;
2) thermolytic cleavage of the intermediate of the formula (B), and optionally
3) purifying the diisocyanate of the formula (A), preferably by fractional distillation, thereby affording the diisocyanate of the formula (A).

In a further aspect, the present invention relates to the diisocyanate of the formula (A) directly prepared by the process according to the invention.

(A)

OCN~~~~~~~NCO
        CO₂R, where R is selected from the group consisting of alkyl, aryl, and combinations thereof, The details and embodiments set out in this description and in the claims as regards the process according to the invention apply by analogy, where applicable, to the diisocyanate directly obtained therewith. To avoid unnecessary repetition, they are not included again here.

INDUSTRIAL APPLICABILITY

The process according to the invention and diisocyanate resulting therefrom can be used for a wide range of applications. For example, the process according to the invention can be employed to produce diisocyanates that are used in polyurethanes. Such polyurethanes are in turn used in many industries. Examples include the production of biocompatible materials for medical applications or of biodegradable products used e.g. in the agricultural sector, or generally of environmentally compatible products from renewable raw materials.

The present invention is elucidated in more detail by the examples which follow, without limiting the subject matter.

EXAMPLES

Gas chromatography (GC): GC was carried out using a Trace 1300 instrument with a 15 m Zebron ZB-1HT column. This was heated from 50 to 270° C. at a rate of 10° C./min. The amine value was determined in accordance with DIN 53176:2002. The acid value was determined in accordance with DIN EN ISO 2114:2002.

Reaction 1: Reaction of Lysine to Form the Urea Adduct of the Formula (C) (Process Step a.2))

A 10 L pressure reactor was charged with 584.4 g (4.0 mol) of L-lysine (process step a.1)). To this was added 600 g of demineralized water, followed by 720.7 g (12.0 mol; 1.5 equivalents based on the primary amine groups of the lysine) of urea and finally 600 g of demineralized water. The stirred reaction mixture was heated to 105° C. and then heated under reflux for 390 min. The reaction mixture was then cooled to room temperature and the water distilled off under reduced pressure. The resulting mixture thus obtained was used in the subsequent reaction 2. Aside from the excess urea, the product is >90% pure according to $^{13}$C NMR.

Reaction 2: Reaction of the Urea Adduct of the Formula (C) to Form the Intermediate of the Formula (B) (Process Step a.3))

To the mixture in the pressure reactor obtained from reaction 1 was added 2209.9 g (48.0 mol) of ethanol. The pressure reactor was heated, with stirring, to 205° C. by means of a W-4010 thermostat unit (Lauda LTH 350). This was accompanied by a rise in pressure; the reactor was maintained at 25 bar overpressure for 5 hours, with the pressure manually vented through a valve from time to time. After 5 hours, the reaction mixture was cooled to room temperature. Volatiles were then removed by distillation under reduced pressure. The purity of the product according to $^{13}$C NMR is approx. 70%. The amine value was <1, the acid value 14 mg KOH/g.

Reaction 3: Thermolytic Cleavage of the Intermediate of the Formula (B) (Process Step 2))

250.0 g of the product obtained in reaction 2 (process step 1)) was mixed with 50 mg of tin(II) chloride dissolved in 50 ml of ethanol and the mixture was heated slowly, with stirring, in an apparatus consisting of a multineck flask fitted with a Liebig condenser, which resulted initially in residual amounts of ethanol distilling off at a bottoms temperature of approx. 80° C. It was then concentrated until molten. The bottoms temperature here was approx. 150° C. The pressure was then reduced to 0.5 mbar and the bottoms temperature gradually and continuously increased. From a bottoms temperature of approx. 190° C., a diisocyanate condensate formed (boiling point approx. 110° C., at the indicated pressure). The bottoms temperature was gradually increased to 235° C. and a total of 60.3 g of diisocyanate was collected (yield: 34% of theory). The ethanol removed ended up in the cold trap. The product was colourless, liquid and approx. 95% pure according to GC.

The invention claimed is:

1. Process for preparing a diisocyanate of the formula (A)

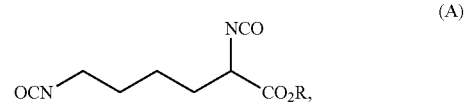

where R is selected from the group consisting of alkyl, aryl, and combinations thereof, comprising the following process steps in the indicated order:

1) Providing an intermediate of the formula (B) with a process using lysine and urea

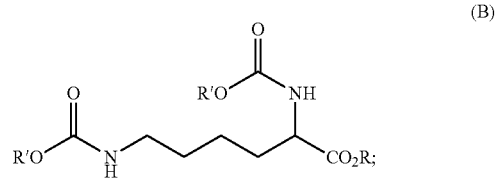

where R and each R' are independently selected from the group consisting of alkyl, aryl, and combinations thereof; and 2) thermolytic cleavage of the intermediate of the formula (B), thereby affording the diisocyanate of the formula (A); and wherein the process further includes one of the following series of process steps prior to process step 1):

either a.1) providing of lysine;
  a.2) reacting the lysine with urea to form a urea adduct of the formula (C)

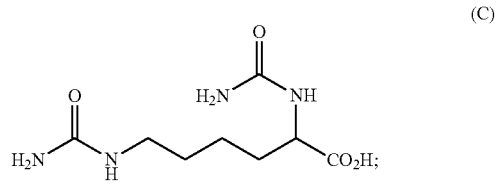 [SMILES: NC(=O)NCCCCC(NC(N)=O)C(=O)O]

and
  a.3) reacting the urea adduct of the formula (C) with an alcohol to form the intermediate of the formula (B);

or b.1) providing of lysine;
  b.2) reacting the lysine with a base to form a lysine salt of the formula (Z);

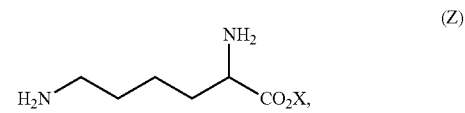

where X is a counterion;

b.3) reacting the lysine salt of the formula (Z) with urea to form a urea salt of the formula (Y);

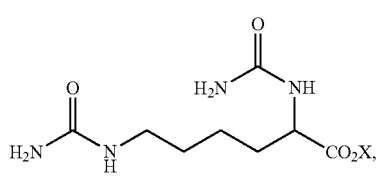
(Y)

where X is a counterion;

b.4) reacting the urea salt of the formula (Y) with an alcohol to form a carbamate of the formula (X)

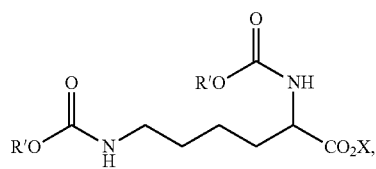
(X)

where each R' is independently selected from the group consisting of alkyl, aryl, and combinations thereof, and X is a counterion;

b.5) reacting the carbamate of the formula (X) with an acid to form the carboxylic acid of the formula (W)

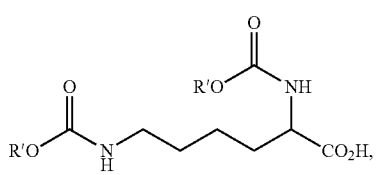
(W)

where each R' is independently selected from the group consisting of alkyl, aryl, and combinations thereof; and b.6) reacting the carboxylic acid of the formula (W) with an alcohol to form the intermediate of the formula (B);

or c.1) providing of lysine;

c.2) reacting the lysine with a base to form a lysine salt of the formula (Z);

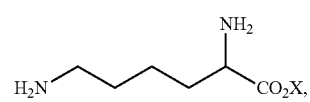
(Z)

where X is a counterion;

c.3) reacting the lysine salt of the formula (Z) with urea to form a urea salt of the formula (Y);

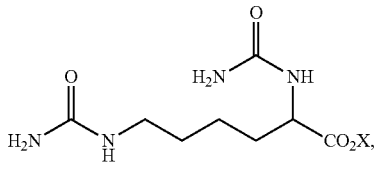
(Y)

where X is a counterion;

c.4) reacting the urea salt of the formula (Y) with an alcohol to form the intermediate of the formula (B).

2. Process according to claim 1, wherein R is selected from the group consisting of C1-C8 alkyl.

3. Process according to claim 1, wherein the thermolytic cleavage is mediated by a mediator.

4. Process according to claim 1, wherein the process includes a further process step 3) after and/or during process step 2):

3) purifying the diisocyanate of the formula (A).

5. Process according to claim 1, wherein the molar ratio of the urea in step a.2) is within a range from 1:1 to 5:1 based on the primary amine groups of the lysine, and the molar ratio of the urea in step b.3) or c.3) is within a range from 1:1 to 5:1 based on the primary amine groups of the lysine salt of the formula (Z).

6. Process according to claim 1, wherein the pressure during the reaction with the alcohol in process step a.3), b.4), b.6), c.4) is for at least part of the time within a range from ≥1 bar.

7. Process according to claim 6, wherein the pressure during the reaction with the alcohol in process step a.3), b.4), b.6), c.4) is within the specified range for 1 to 20 hours.

8. Process according to claim 1, wherein the reaction with the alcohol in process step a.3), b.4), b.6), c.4) is carried out at least at a temperature from 150 to 300° C.

9. Process according to claim 8, wherein the reaction with the alcohol in process step a.3), b.4), b.6), c.4) is conducted within the specified temperature range for a period of 1 to 20 hours.

10. Process according to claim 1, wherein the molar ratio of the alcohol in step a.3) based on the urea adduct of the formula (C) is within a range from 2:1 to 100:1, the molar ratio of the alcohol in step b.6) based on the carboxylic acid of the formula (W) is within a range from 2:1 to 100:1, and the molar ratio of the alcohol in step c.4) based on the urea salt of the formula (Y) is within a range from 2:1 to 100:1.

11. Process according to claim 1, wherein the reaction in process steps a.2), b.3) and c.3) is carried out in a polar solvent.

12. Process according to claim 2, wherein R is selected from the group consisting methyl, ethyl, isopropyl, n-propyl, n-butyl, isobutyl, sec-butyl and tert-butyl.

13. Process according to claim 3, wherein the thermolytic cleavage is mediated by a metal-based catalyst.

14. Process according to claim 13, wherein the metal-based catalyst is a tin(II) salt.

15. Process according to claim 4, wherein the diisocyanate of the formula (A) is purified by fractional distillation.

16. Process according to claim 6, wherein the pressure during the reaction with the alcohol in process step a.3), b.4), b.6), c.4) is for at least part of the time within a range from 1 to 25 bar.

17. Process according to claim 7, wherein the pressure during the reaction with the alcohol in process step a.3), b.4), b.6), c.4) is within the specified range 4 to 6 hours.

18. Process according to claim 8, wherein the reaction with the alcohol in process step a.3), b.4), b.6), c.4) is carried out at least at a temperature from 190 to 220° C.

19. Process according to claim 9, wherein the reaction with the alcohol in process step a.3), b.4), b.6), c.4) is conducted within the specified temperature range for a period of 4 to 6 hours.

20. Process according to claim 11, wherein the polar solvent is water.

* * * * *